US00PP34875P2

(12) United States Plant Patent
van Sambeek

(10) Patent No.: US PP34,875 P2
(45) Date of Patent: Dec. 27, 2022

(54) ***PENSTEMON* PLANT NAMED 'DOPENSPRINIG'**

(50) Latin Name: *Penstemon barbatus*
Varietal Denomination: Dopensprinig

(71) Applicant: DUMMEN GROUP B.V., De Lier (NL)

(72) Inventor: Ellen van Sambeek, Oegstgeest (NL)

(73) Assignee: DÜMMEN GROUP B.V., DeLier (NL)

( * ) Notice: Subject to any disclaimer, the term of this patent is extended or adjusted under 35 U.S.C. 154(b) by 0 days.

(21) Appl. No.: 17/839,356

(22) Filed: Jun. 13, 2022

(51) Int. Cl.
*A01H 5/02* (2018.01)
*A01H 6/68* (2018.01)

(52) U.S. Cl.
USPC ..... Plt./465
CPC ..... *A01H 6/68* (2018.05)

(58) Field of Classification Search
USPC ..... Plt./465
CPC ..... A01H 6/68; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Penstemon* plant named 'Dopensprinig', characterized by its upright plant habit; vigorous growth habit and rapid growth rate; freely branching habit; freely flowering habit; long flowering period; relatively large dark purple-colored flowers; and good garden performance.

1 Drawing Sheet

Botanical designation: *Penstemon barbatus.*
Cultivar denomination: 'DOPENSPRINIG'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Feb. 18, 2022, application number 2022/0500. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Penstemon* plant, botanically known as *Penstemon barbatus* and hereinafter referred to by the name 'Dopensprinig'.

The new *Penstemon* plant is a product of a planned breeding program conducted by the Inventor in Aalsmeer, The Netherlands. The objective of the breeding program was to create new freely-branching *Penstemon* plants with attractive flower color.

The new *Penstemon* plant originated from an open-pollination in July, 2016 in Aalsmeer, The Netherlands, of a proprietary selection of *Penstemon barbatus* identified as code number PE14-000053-014, not patented, as the female, or seed, parent with an unknown selection of *Penstemon barbatus* as the male, or pollen, parent. The new *Penstemon* plant was discovered and selected by the Inventor as a single flowering plant from within the progeny of the stated open-pollination in a controlled environment in Aalsmeer, The Netherlands in May, 2017.

Asexual reproduction of the new *Penstemon* plant by terminal vegetative cuttings in a controlled environment in Aalsmeer, The Netherlands since June, 2017 has shown that the unique features of this new *Penstemon* plant are stable and reproduced true to type in successive generations.

SUMMARY OF THE INVENTION

Plants of the new *Penstemon* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dopensprinig'. These characteristics in combination distinguish 'Dopensprinig' as a new and distinct *Penstemon* plant:

1. Upright plant habit.
2. Vigorous growth habit and rapid growth rate.
3. Freely branching habit.
4. Freely flowering habit.
5. Long flowering period.
6. Relatively large dark purple-colored flowers.
7. Good garden performance.

Plants of the new *Penstemon* differ primarily from plants of the female parent selection in flower color as plants of the new *Penstemon* have dark purple-colored flowers whereas plants of the female parent selection have pink-colored flowers.

Plants of the new *Penstemon* can be compared to plants of *Penstemon schmidel* 'Marble Riding Hood', disclosed in U.S. Plant Pat. No. 23,098. In side-by-side comparisons, plants of the new *Penstemon* and 'Marble Riding Hood' differ in the following characteristics:

1. Plants of the new *Penstemon* are more freely branching than plants of 'Marble Riding Hood'.
2. Flowers of plants of the new *Penstemon* are dark purple in color whereas flowers of plants of 'Marble Riding Hood' are light red purple and white in color.

BRIEF DESCRIPTION OF THE PHOTOGRAPH

The accompanying colored photograph illustrates the overall appearance of the new *Penstemon* plant showing the colors as true as it is reasonably possible to obtain in colored reproductions of this type. Colors in the photograph may differ slightly from the color values cited in the detailed botanical description which accurately describe the colors of the new *Penstemon* plant. The photograph is a side perspective view of typical flowering plant of 'Dopensprinig' grown in a container.

DETAILED BOTANICAL DESCRIPTION

The aforementioned photograph and following observations, measurements and values describe plants grown during the summer in 17-cm containers initially in a glass-covered greenhouse and finished in an outdoor nursery in Aalsmeer, The Netherlands and under cultural practices typical of commercial *Penstemon* production. During the production of the plants, day temperatures averaged 21° C. and night temperatures averaged 15° C. Plants were 22 weeks old when the photograph and detailed description were taken. In the following description, color references are made to The Royal Horticultural Society Colour Chart, Second Edition, except where general terms of ordinary dictionary significance are used.

Botanical classification: *Penstemon barbatus* 'Dopensprinig'.

Parentage:

*Female, or seed, parent*.—Proprietary selection of *Penstemon barbatus* identified as code number PE14-000053-014, not patented.

*Male, or pollen, parent*.—Unknown selection of *Penstemon barbatus*, not patented.

Propagation:

*Type*.—By vegetative cuttings.

*Time to initiate roots, summer*.—About 12 days at temperatures about 26° C.

*Time to initiate roots, winter*.—About 16 days at temperatures about 23° C.

*Time to produce a rooted young plant, summer*.—About 16 days at temperatures about 23° C.

*Time to produce a rooted young plant, winter*.—About 20 days at temperatures about 18° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; upright plant habit; vigorous growth habit and rapid growth rate.

*Plant height*.—About 40 cm.

*Plant width* (*spread*).—About 34 cm.

*Lateral branches*.—Quantity of lateral branches: Freely branching habit, about 14 lateral branches develop per plant. Length: About 38 cm. Diameter: About 5 mm. Internode length: About 5 cm. Strength: Strong. Aspect: Upright to about 30° from vertical. Texture and luster: Smooth, glabrous; glossy. Color, developing: Close to 144B. Color, developed: Close to 144A.

Leaf description:

*Arrangement*.—Opposite, simple; decussate and sessile.

*Length*.—About 11.5 cm.

*Width*.—About 2 cm.

*Shape*.—Linear to lanceolate.

*Apex*.—Acute.

*Base*.—Cuneate.

*Margin*.—Entire.

*Texture and luster, upper and lower surfaces*.—Smooth, glabrous; glossy.

*Venation pattern*.—Pinnate.

*Color*.—Developing leaves, upper surface: Close to 146A. Developing leaves, lower surface: Close to 146B. Fully expanded leaves, upper surface: Close to 147A; venation, close to 144A. Fully expanded leaves, lower surface: Close to 147A; venation, close to 145A.

Flower description:

*Flower shape, arrangement and flowering habit*.—Single bi-labiate flowers arranged on terminal racemes; flowers face mostly outwardly; freely flowering with about 20 flowers developing per inflorescence and about 770 flowers developing per plant during the flowering season.

*Fragrance*.—Faintly fragrant; pleasant.

*Time to flower*.—Early flowering habit, plants begin to flower about 14 weeks after planting.

*Natural flowering season*.—Long flowering period, plants flower for about eight to ten weeks during the summer in The Netherlands; flowers not persistent.

*Flower buds*.—Length: About 2.5 cm. Diameter: About 6 mm. Shape: Elongate ovoid. Texture and luster: Smooth, glabrous; glossy. Color: Close to 77A.

*Inflorescence height*.—About 26 cm.

*Inflorescence diameter*.—About 8 cm.

*Flower width* (*horizontal*).—About 1.5 cm.

*Flower length* (*vertical*).—About 2 cm.

*Flower depth*.—About 3 cm.

*Flower throat diameter*.—About 1 cm.

*Flower tube length*.—About 2 cm.

*Flower tube diameter*.—About 9 mm.

*Petals*.—Arrangement: Five, fused into a tube; bilabiate, upper lip with two upper petals and lower lip with three lower petals. Lobe length, upper and lower lips: About 1 cm. Lobe width, upper and lower lips: About 5 mm. Lobe shape: Oblong. Lobe apex: Obtuse. Lobe margin: Entire; not undulate. Lobe texture and luster, upper surface: Smooth, glabrous; matte. Lobe texture and luster, lower surface: Pubescent; glossy. Throat, texture: Smooth, glabrous.

Tube, texture: Pubescent. Color: Lobes, when opening, upper and lower surfaces: Close to 77A. Lobes, fully opened, upper surface: Upper lip, close to 79B and lower lip, close to 77A; venation, close to 79A; color does not change with subsequent development. Lobes, fully opened, upper surface: Upper lip, close to 79B and lower lip, close to 77A; venation, close to 77A; color does not change with subsequent development. Flower throat: Close to 77A; venation, close to 79A. Flower tube: Close to 77A; venation, close to 77A.

*Sepals*.—Arrangement: Five sepals fused in a single whorl. Length: About 6 mm. Width: About 3 mm. Shape: Ovate. Apex: Acuminate. Margin: Entire. Texture and luster, upper and lower surfaces: Smooth, glabrous; glossy. Color: When opening and fully developed, upper surface: Close to 143A. When opening and fully developed, lower surface: Close to 143A.

*Peduncles*.—Length: About 2.5 cm. Diameter: About 2 mm. Aspect: About 5° from stem axis. Strength: Moderately strong. Texture and luster: Smooth, glabrous; glossy. Color: Close to 144A.

*Pedicels*.—Length: About 1 cm. Diameter: About 1 mm. Aspect: Upright to about 30° from peduncle axis. Strength: Weak. Texture and luster: Smooth, glabrous; glossy. Color: Close to 144A tinged with close to 77A.

*Reproductive organs*.—Stamens: Quantity per flower: Four. Filament length: About 2.5 cm. Filament color: Close to 155D. Anther size: About 1 mm by 4 mm. Anther shape: Oblong. Anther color: Close to 158A. Pollen amount: Abundant. Pollen color: Close to 155A. Pistils: Quantity per flower: One. Pistil length: About 2.5 cm. Style length: About 2.1 cm. Style color: Close to 77B and 155D. Stigma diameter: About 0.5 mm. Stigma shape: Capitate. Stigma color: Close to 155D. Ovary color: Close to 144A.

*Seeds and fruits*.—To date, seed and fruit development have not been observed on plants of the new *Penstemon*.

Garden performance: Plants of the new *Penstemon* have been observed to have good garden performance and tolerate rain, wind and temperatures ranging from −25° C. to 35° C. and to be suitable for USDA Hardiness Zone 5.

Pathogen & pest resistance: To date, plants of the new *Penstemon* have not been observed to be resistant to pathogens and pests common to *Penstemon* plants.

It is claimed:

1. A new and distinct *Penstemon* plant named 'Dopensprinig' as illustrated and described.

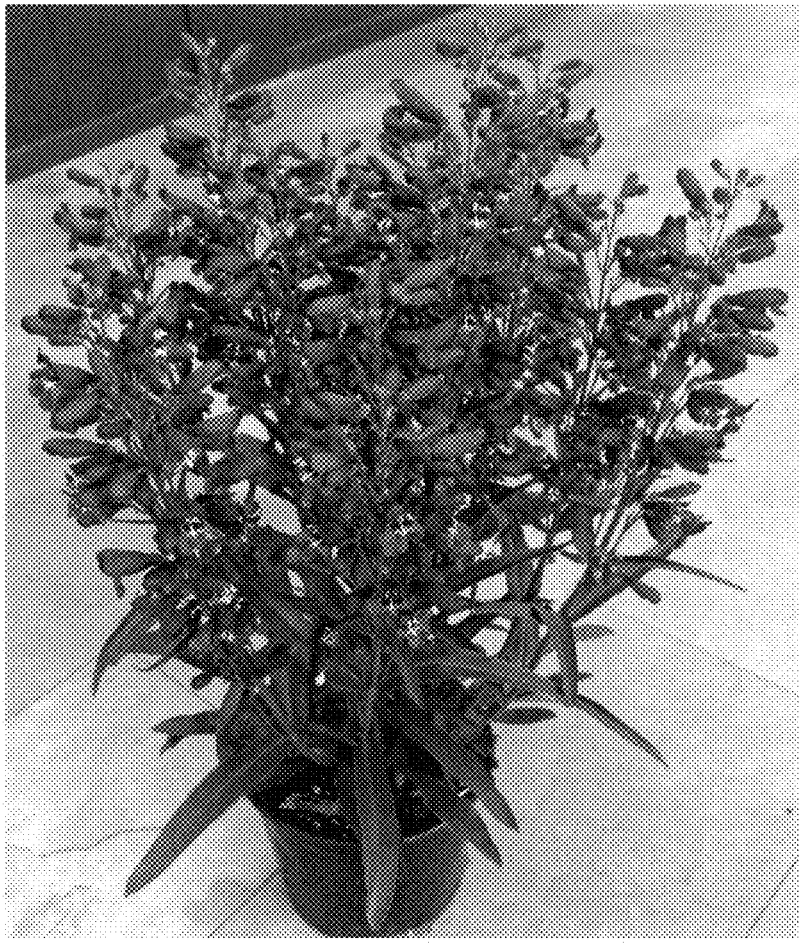

* * * * *